United States Patent
Kelliher et al.

(10) Patent No.: US 9,079,847 B2
(45) Date of Patent: Jul. 14, 2015

(54) PROCESS FOR PREPARING AND PURIFYING FATTY ACIDS

(75) Inventors: Adam Kelliher, London (GB); Angus Morrison, Isle of Lewis (GB); Phil Knowles, Cumbria (GB)

(73) Assignee: BASF PHARMA (CALLANISH) LIMITED (GB)

( * ) Notice: Subject to any disclaimer, the term of this patent is extended or adjusted under 35 U.S.C. 154(b) by 376 days.

(21) Appl. No.: 13/574,634

(22) PCT Filed: Jan. 27, 2011

(86) PCT No.: PCT/GB2011/000104
§ 371 (c)(1),
(2), (4) Date: Sep. 25, 2012

(87) PCT Pub. No.: WO2011/092467
PCT Pub. Date: Aug. 4, 2011

(65) Prior Publication Data
US 2013/0150602 A1    Jun. 13, 2013

(30) Foreign Application Priority Data

Jan. 27, 2010   (GB) .................................. 1001345.6

(51) Int. Cl.
| | | |
|---|---|---|
| C07C 51/00 | (2006.01) |
| C07C 51/487 | (2006.01) |
| C07C 51/41 | (2006.01) |
| C07C 51/42 | (2006.01) |
| C07C 51/48 | (2006.01) |
| C07C 51/38 | (2006.01) |

(52) U.S. Cl.
CPC .............. *C07C 51/487* (2013.01); *C07C 51/38* (2013.01); *C07C 51/41* (2013.01); *C07C 51/412* (2013.01); *C07C 51/42* (2013.01); *C07C 51/48* (2013.01)

(58) Field of Classification Search
CPC .... C07C 51/097; C07C 51/00; C07C 403/20; C07C 2101/16; C11C 1/04
USPC .................................. 554/154, 161, 195, 202
See application file for complete search history.

(56) References Cited

U.S. PATENT DOCUMENTS

| | | | |
|---|---|---|---|
| 2,228,925 A | 1/1941 | Martin |
| 4,097,507 A | 6/1978 | Person |
| 5,034,509 A | 7/1991 | Ravaska |
| 5,252,333 A | 10/1993 | Horrobin |
| 5,422,115 A | 6/1995 | Horrobin |
| 6,310,227 B1 | 10/2001 | Sarama et al. |
| 8,182,553 B2 | 5/2012 | Frykeras et al. |
| 8,304,515 B2 | 11/2012 | Tonelli et al. |
| 2009/0081578 A1 | 3/2009 | Burleva et al. |
| 2009/0093648 A1 | 4/2009 | Purtle et al. |
| 2011/0021796 A1 | 1/2011 | Saebo |

FOREIGN PATENT DOCUMENTS

| | | |
|---|---|---|
| CA | 2156155 A1 | 8/1994 |
| CN | 1718702 A1 | 1/2006 |
| CN | 101481637 A1 | 7/2009 |
| GB | 0942452 A | 11/1963 |
| GB | 1225506 A | 3/1971 |
| GB | 1433156 A | 4/1976 |
| JP | 60142940 A1 | 7/1985 |
| JP | 2000004894 A1 | 11/2000 |
| WO | 0073254 A1 | 12/2000 |

OTHER PUBLICATIONS

Meyer, H et al. "Uber die Lignocerinsaure", Monatshefte Fuer Chemie, vol. 34, 1913, pp. 1113-1142.*
Xue, Gang; Liu, Fengxia; Wang, Ying, "Optimization of Synthetic Conditions of the Preparation of Dihomo-Linolenic Acid from Linolenic Acid," Journal American Oil Chemical Society, vol. 86, 2009, pp. 77-82.*
Meyer, Hans; Brod, L.; Soyka, W., "Uber die Lignocerinsaure," Monatshefte fuer Chemie, vol. 34, 1913, pp. 1113-1142.
Bleyberg, Werner; Ulrich, Helmut, "Synthese hochmolekularer Fettsauren und ihrer Anhydride," Chemisch Berichte, vol. 64, No. 9, 1931, pp. 2504-2513.
Schwab, John M.; Habib, Asis, Klassen, John B., "A Thorough Study of the Stereochemical Consequences of the Hydration/Dehydration /Reaction Catalyzed by B-Hydroxydecanoyl Thioester Dehydrase," Journal of the American Chemical Society, vol. 108, No. 17, 1986, pp. 5304-5308.
Liang, Yong-Tao; Wei, Feng Ping; Li Gurying; Wang, En-Si, "Chemoenzymic Synthesis of Prostaglandin E1," Acta Scientiarum Naturalium Universitatis Jilinensis, vol. 2, 2001, pp. 77-80.
Kawashima, Hiroshi; Akimoto, Kengo; Higashiyama, Kenichi; Fujikawa, Shigeaki; Shimizu, Sakayu, "Industcrial Production of Dihomo-liolenic acid by D5 Desaturase-defective Mutant of *Mortierella* alpina 1S-4 Fungus," Journal American Oil Chemical Society, vol. 77, 2000, pp. 1135-1139.
Hethelyib, Eva, "Novenyi prosztaglandinok valtozatossaga, analitikaja es farmakologiaja," Olaj-Szappan-Kozmetica, vol. 52(3), 2003, 146-154.
Kuklev, D. V.; Popkov, A. A.; Kas'Yanov, S. P.; Akulin, V. N.; Bezuglov, V. V., "Synthesis of C2-Elongated Polyunsaturated Fatty Acids," Russian Journal of Bioorganic Chemistry, vol. 22, 1996, pp. 219-222.
Shafu, Zhang; Jiating, Sun, Effects of Chinese Ginseng Stem Leaves Saponins Avoidance Conditioning and Descrination Learning, Journal of Shenyang college of Pharmacy, 1988, vol. 5, No. 4, pp. 275-278.
Sun, et al., J.N. Bethune Univ. Med. Sci., vol. 21, No. 4, 1995, pp. 427-428.

\* cited by examiner

*Primary Examiner* — Deborah D Carr
(74) *Attorney, Agent, or Firm* — Luedeka Neely Group, PC

(57) ABSTRACT

There is provided a process for purifying a fatty acid, which process comprises reacting a fatty acid with a lithium salt in a first solution and under conditions to allow formation of a precipitate of a lithium salt of the fatty acid; isolating the precipitate; dissolving the precipitate in a second solution followed by separation of the organic and aqueous layers so formed; and evaporating the organic layer to isolate the purified fatty acid. There is also provided a process for increasing the length of a fatty acid, and the use of a lithium salt to purify a fatty acid.

18 Claims, No Drawings

PROCESS FOR PREPARING AND PURIFYING FATTY ACIDS

BACKGROUND TO THE INVENTION

The invention is concerned with the preparation and purification of fatty acids. Fatty acids are aliphatic monocarboxylic acids which are commonly derived from animal and vegetable sources. As well as being a source of energy, fatty acids play many other key roles in the body. They can help to regulate healthy lipid levels, and are involved in inflammatory responses. They are also important in the blood, regulating clotting and blood pressure.

A number of fatty acids can be synthesised by the body in vivo. However some, designated "essential fatty acids", cannot. Essential fatty acids include the short chain polyunsaturated fatty acids (SC-PUFAs) linoleic acid and α-linolenic acid, as well as long chain polyunsaturated fatty acids (LC-PUFAs) which can be prepared from these SC-PUFAs. These two categories are generally split into two further categories, the ω-3 (or "Omega 3") fatty acids, and the ω-6 (or "Omega 6") fatty acids. Representative LC-PUFAs include the ω-3 fatty acids eicosapentaenoic acid (EPA) and docosahexaenoic acid (DHA), and the ω-6 fatty acids gamma-linolenic acid (GLA), dihomo-gamma-linolenic acid (DGLA) and arachidonic acid (AA).

As essential fatty acids cannot be synthesised by the body in vivo they must be provided by diet. There is therefore a need to develop and improve processes and techniques for isolating and purifying these essential fatty acids. There is also a need to develop and improve processes for converting essential fatty acids into other fatty acids, in order to provide a wide range of compounds and supplements necessary to meet the requirements of individuals. Further, a number of PUFA products are needed in purified form as they are pharmaceutically active.

Novel processes for purifying fatty acids have now been found which can lead to simplified production and/or increased purity and/or easier scale-up of process. The novel purification processes can be used in isolation on a prepared fatty acid, or can be incorporated into a longer process for the preparation of said fatty acid. These processes help to remove non-acidic impurities from the fatty acids.

SUMMARY OF THE INVENTION

The invention provides the use of a lithium salt to purify a fatty acid.

The invention further provides a process for purifying a fatty acid, which process comprises:
(a) reacting a fatty acid with a lithium salt in a first solution and under conditions to allow formation of a precipitate of a lithium salt of the fatty acid;
(b) isolating the precipitate;
(c) dissolving the precipitate in a second solution which is capable of generating two immiscible layers upon dissolution of the precipitate, the two immiscible layers being an organic layer and an aqueous acidic layer;
(d) separating the two immiscible layers formed upon dissolution of the precipitate; and
(e) evaporating the organic layer to isolate the purified fatty acid.

There is also provided a process for preparing a fatty acid, which process comprises:
(a) decarboxylating a malonic acid derivative of formula R—$CH_2CH(CO_2H)_2$, wherein R is a fatty acid residue, to form a fatty acid of formula $RCH_2CH_2CO_2H$;
(b) subjecting the fatty acid thus prepared to a process for purifying a fatty acid as described above.

There is further provided a process for extending the length of a fatty acid, which process comprises:
(a) reducing a fatty acid of formula R—$CO_2H$ or a fatty acid ester of formula R—$CO_2R^1$, wherein R is a fatty acid residue and $R^1$ is a $C_{1-6}$ alkyl group, to an alcohol of formula R—$CH_2OH$;
(b) sulfonating the alcohol to form a sulfonate of formula R—$CH_2OSO_2R^2$, wherein $R^2$ is a $C_{1-6}$ alkyl or $C_{6-10}$ aryl group;
(c) reacting the sulfonate with a malonate ester derivative and hydrolysing the resulting product to form a malonic acid derivative of formula R—$CH_2CH(CO_2H)_2$;
(d) decarboxylating the malonic acid derivative to form a fatty acid of formula R—$CH_2CH_2CO_2H$; and
(e) subjecting the fatty acid thus prepared to a process for purifying a fatty acid as described above.

DETAILED DESCRIPTION OF THE INVENTION

As used herein, a $C_{1-6}$ alkyl group is a linear or branched alkyl group containing from 1 to 6 carbon atoms, for example a $C_{1-4}$ alkyl group containing from 1 to 4 carbon atoms. Examples of $C_{1-4}$ alkyl groups include methyl, ethyl, n-propyl, i-propyl, n-butyl, i-butyl and t-butyl. For the avoidance of doubt, where two alkyl moieties are present they may be the same or different.

As used herein, a $C_2$-$C_4$ alkenyl group is a linear or branched alkenyl group having at least one double bond of either cis or trans configuration where applicable and containing from 2 to 4 carbon atoms, for example —CH=$CH_2$ or —$CH_2$—CH=$CH_2$; —$CH_2$—$CH_2$—CH=$CH_2$, —$CH_2$—CH=CH—$CH_3$, —CH=C($CH_3$)—$CH_3$ and —$CH_2$—C($CH_3$)=$CH_2$, preferably a $C_2$ alkenyl group having 2 carbon atoms. For the avoidance of doubt, where two alkenyl groups are present in a compound of the present invention, they may be the same or different.

As used herein, a halogen atom is typically chlorine, fluorine, bromine or iodine.

As used herein, a $C_1$-$C_4$ alkoxy group or $C_2$-$C_4$ alkenyloxy group is typically a said $C_1$-$C_4$ alkyl group or a said $C_2$-$C_4$ alkenyl group respectively which is attached to an oxygen atom.

A haloalkyl, haloalkenyl, haloalkoxy or haloalkenyloxy group is typically a said alkyl, alkenyl, alkoxy or alkenyloxy group respectively which is substituted by one or more said halogen atoms. Typically, it is substituted by 1, 2 or 3 said halogen atoms. Preferred haloalkyl and haloalkoxy groups include perhaloalkyl and perhaloalkoxy groups, such as —$CX_3$ and —$OCX_3$ wherein X is a said halogen atom, for example chlorine and fluorine.

As used herein, a $C_1$-$C_4$ alkylthio or $C_2$-$C_4$ alkenylthio group is typically a said $C_1$-$C_4$ alkyl group or a $C_2$-$C_4$ alkenyl group respectively which is attached to a sulfur atom, for example —S—$CH_3$.

As used herein, a $C_1$-$C_4$ hydroxyalkyl group is a $C_1$-$C_4$ alkyl group substituted by one or more hydroxy groups. Typically, it is substituted by one, two or three hydroxy groups. Preferably, it is substituted by a single hydroxy group.

As used herein, a $C_{6-10}$ aryl group is a phenyl group or a naphthyl group. For the avoidance of doubt, where two aryl groups are present they may be the same or different.

Unless otherwise specified, $C_{6-10}$ aryl groups can be unsubstituted or substituted with 1, 2, 3 or 4 substituents which are the same or different and are chosen from halogen atoms and $C_{1-4}$ alkyl, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, mercapto, cyano, nitro, $C_{1-4}$ hydroxyalkyl, $C_{2-4}$ hydroxyalkenyl, $C_{1-4}$ alkylthio, $C_{2-4}$ alkenylthio and —NR"R" groups wherein each R' and R" is the same or different and represents hydrogen or $C_{1-4}$ alkyl. Where a substituent on an aryl group is selected from phenyl, carbocyclyl, heterocyclyl, heteroaryl, —COR$^A$, —SO$_2$R$^A$, —CONH$_2$, —SO$_2$NH$_2$, —CONHR$^A$, —SO$_2$NHR$^A$, —CONR$^A$R$^B$ and —SO$_2$NR$^A$R$^B$, preferably only one such substituent is present. Preferably the $C_{6-10}$ aryl groups are unsubstituted or substituted with 1 or 2, preferably 1, unsubstituted substituent. Preferred substituents include $C_{1-4}$ alkyl, $C_{1-4}$ alkoxy, $C_{1-4}$ alkylthio and hydroxyl groups. More preferred substituents include halogen atoms, and $C_{1-4}$ alkyl, $C_{1-2}$ alkoxy and hydroxy groups. Most preferably the aryl groups are unsubstituted.

As used herein, a $C_{3-7}$ carbocyclic group is a non-aromatic saturated or unsaturated hydrocarbon ring having from 3 to 7 carbon atoms. Preferably it is a saturated or mono-unsaturated hydrocarbon ring (i.e. a cycloalkyl moiety or a cycloalkenyl moiety) having from 3 to 7 carbon atoms, more preferably having from 3 to 6 carbon atoms. Examples include cyclopropyl, cyclobutyl, cyclopentyl and cyclohexyl and their mono-unsaturated variants, more particularly cyclopentyl and cyclohexyl. A $C_{3-7}$ carbocyclyl group or moiety also includes $C_{3-7}$ carbocyclyl groups or moieties described above but wherein one or more ring carbon atoms are replaced by a group —C(O)—. Preferably the carbocyclic groups do not have any ring carbon atoms replaced by a group —C(O)—.

As used herein, a 5- or 6-membered heterocyclyl group is a non-aromatic, saturated or unsaturated $C_{5-6}$ carbocyclic ring in which one or more, for example 1, 2, 3 or 4, of the carbon atoms are replaced with a moiety selected from N, O, S, S(O) and S(O)$_2$, and wherein one or more of the remaining carbon atoms is optionally replaced by a group —C(O)— or —C(S)—. When one or more of the remaining carbon atoms is replaced by a group —C(O)— or —C(S)—, preferably only one or two (more preferably two) such carbon atoms are replaced. Suitable heterocyclyl groups include pyrrolidinyl, pyrrolinyl, pyrrolyl, tetrahydrofuranyl, dihydrofuranyl, furanyl, tetrahydrothiophenyl, dihydrothiophenyl, thiophenyl, imidazolidinyl, pyrazolidinyl, imidazolyl, imidazolinyl, pyrazolyl, pyrazolinyl, oxazolidinyl, isoxazolidinyl, oxazolyl, oxazolinyl, isoxazolyl, isoxazolinyl, thiazolidinyl, isothiazolidinyl, thiazolyl, thiazolinyl, isothiazolyl, isothiazolinyl, dioxolanyl, oxathiolanyl, dithiolanyl and thiophenyl.

As used herein the term "salt" includes base addition, acid addition and quaternary salts. Exemplary salts include those formed with bases such as alkali metal hydroxides, e.g. lithium, sodium and potassium hydroxides; alkaline earth metal hydroxides e.g. calcium, barium and magnesium hydroxides; with organic bases e.g. N-methyl-D-glucamine, choline tris(hydroxymethyl)amino-methane, L-arginine, L lysine, N-ethyl piperidine, dibenzylamine and the like.

Unless otherwise defined, as used herein the term "fatty acid" represents a $C_{4-26}$ aliphatic monocarboxylic acid, more preferably a $C_{10-24}$ aliphatic monocarboxylic acid, more preferably a $C_{14-24}$ aliphatic monocarboxylic acid. The fatty acids which are the products of the processes mentioned herein preferably contain from 16 to 24 carbon atoms. Fatty acids are derived from or contained in many sources. For example they can be derived from or contained in esterified form in, an animal or vegetable fat, oil, or wax. They can also be prepared from other, shorter chain fatty acids in accordance with one of the processes of the invention.

The fatty acids used in the invention have hydrocarbon chains which are straight or branched. Preferably the hydrocarbon chains are straight. The hydrocarbon chains can also contain, within the chain, a $C_{3-7}$ carbocyclyl or 3- to 7-membered heterocyclyl ring. Preferably, however, the hydrocarbon chains do not contain carbocyclic or heterocyclyl rings. The hydrocarbon chains can also contain, within their backbone, one or more, preferably one, oxygen atom. Preferably, however, the hydrocarbon chains do not contain oxygen atoms.

As used herein, the term "fatty acid ester" represents an ester of a fatty acid described above. Preferably the fatty acid ester is an alkyl ester with the alkyl group being a $C_{1-6}$ alkyl group. Preferred fatty acid esters thus include esters of formula R—CO$_2$R$^1$ wherein R is a fatty acid residue and R$^1$ is a $C_{1-6}$ alkyl group. Preferably R$^1$ is unsubstituted. Preferably R$^1$ is a $C_{1-4}$ alkyl group, more preferably a methyl or ethyl group, most preferably an ethyl group.

As used herein, the term "fatty acid residue" refers to the hydrocarbyl tail of a fatty acid as described above. Specifically the fatty acid residue corresponds to a fatty acid excluding the terminal carboxylic acid group. Accordingly, a fatty acid of formula R—CO$_2$H contains the fatty acid residue R. In the following discussion the fatty acid residue will be described with reference to the fatty acid from which it is derived. For the avoidance of doubt, the fatty acid residue can also be derived from a fatty acid ester of formula R—CO$_2$R' where R' is the alkyl group of the ester.

Preferably R is a fatty acid residue formed from a fatty acid containing 14 to 22 carbon atoms, more preferably from 16 to 22 carbon atoms, most preferably from 18 to 20 carbon atoms.

Preferably R is a fatty acid residue formed from a fatty acid which is fully saturated or contains from 1 to 6 centers of unconjugated unsaturation. The centers of unconjugated unsaturation represent olefinic (—CH═CH—) and/or acetylenic (—C≡C—) groups which are arranged such that their delocalised electrons are not in conjugation with another centre of unsaturation. Preferably the fatty acid contains 2, 3, 4, 5 or 6 more preferably 2, 3, 4 or 5, more preferably 2, 3 or 4, most preferably 3 or 4 centres of unconjugated unsaturation. It is preferred that the centers of unconjugated unsaturation are olefinic groups. As will be appreciated, for a hydrocarbyl chain of a given length, there may be multiple arrangements of the unconjugated unsaturation along the chain. For example, fatty acids designated as ω-3 (or "Omega 3") fatty acids contain a final carbon-carbon double bond in the n−3 position, i.e. the third bond from the methyl end of the fatty acid is a carbon-carbon double bond. Fatty acids designated as ω-6 (or "Omega 6") fatty acids contain a final carbon-carbon double bond in the n−6 position, i.e. the sixth bond from the methyl end of the fatty acid is a carbon-carbon double bond. Preferably R is a fatty acid residue formed from an ω-3 or ω-6 fatty acid, also referred to as ω-3 fatty acid residues or ω-6 fatty acid residues.

Most preferred R groups are those derived from ω-3 or ω-6 fatty acids having from 16 to 22 carbon atoms, more preferably from 18 to 20 carbon atoms, and containing from 2 to 5, more preferably 2 to 4, most preferably 3 or 4, unconjugated olefinic groups. Exemplary fatty acid residues include the $C_{17}H_{29}$-residue from gamma-linolenic acid, the $C_{19}H_{29}$-residue from eicosapentaenoic acid, the $C_{17}H_{27}$-residue from stearidonic acid, the $C_{17}H_{31}$-residue from linoleic acid, and the $C_{17}H_{29}$-residue from alpha-linolenic acid. Preferred fatty acid residues are the $C_{17}H_{29}$-residue from gamma-linolenic acid, the $C_{19}H_{29}$-residue from eicosapentaenoic acid, and the $C_{17}H_{27}$-residue from stearidonic acid. Most preferred fatty acid residues are the $C_{17}H_{29}$-residue from gamma-linolenic acid, and the $C_{19}H_{29}$-residue from eicosapentaenoic acid. For the avoidance of doubt, the structures of gamma-linolenic acid, eicosapentaenoic acid and stearidonic acid are as follows:

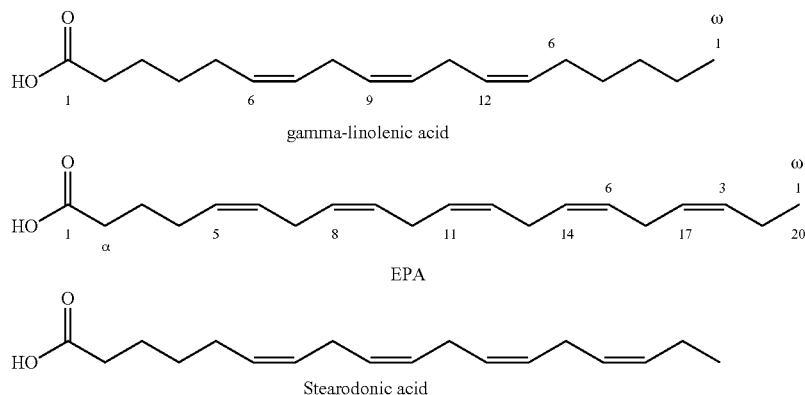

gamma-linolenic acid

EPA

Stearodonic acid

The fatty acids which are purified in accordance with the purification process of the invention are preferably $C_{16-24}$ fatty acids. They are preferably prepared via a chain extension process (e.g. via a malonate chain extension process) from the fatty acids of formula $R—CO_2H$ where R is a fatty acid residue described above. Accordingly, the fatty acids which are purified in accordance with the invention are preferably of formula $R—CH_2—CH_2—CO_2H$, generated by a chain extension process of a fatty acid of formula $R—CO_2H$. The group R in the fatty acids of formula $R—CH_2—CH_2—CO_2H$ is preferably as described earlier.

These fatty acids which are purified in accordance with the purification process of the invention are preferably ω-3 or ω-6 fatty acids having from 16 to 24 carbon atoms, more preferably from 20 to 22 carbon atoms, and containing 2, 3, 4, 5 or 6, more preferably 2, 3, 4 or 5, more preferably 2, 3 or 4, most preferably 3 or 4, unconjugated olefinic groups. Exemplary fatty acids include the ω-6 fatty acids dihomo-gamma-linolenic acid (DGLA) and eicosadienoic acid, and the ω-3 fatty acids docosapentaenoic acid (DPA, sometimes referred to as DEPA), eicosatetraenoic acid (ETA) and eicosatrienoic acid. A preferred ω-6 fatty acid is dihomo-gamma-linolenic acid (DGLA). Preferred ω-3 fatty acids are docosapentaenoic acid (DPA) and eicosatetraenoic acid (ETA), more preferably docosapentaenoic acid (DPA). For the avoidance of doubt, the structures of DGLA (ω-6), DPA (ω-3) and ETA (ω-3) are as follows, with carbon atom numbering being included for information purposes:

As described earlier, the invention provides the use of a lithium salt to purify a fatty acid.

Typically, the lithium salt is other than lithium aluminium hydride. Preferably, the lithium salt is not hydride-yielding.

Typically, the fatty acid is a single fatty acid as defined above, i.e. the fatty acid is not a mixture of fatty acids. Thus, typically, the lithium salt is added to a mixture of the single fatty acid and non-acidic impurities. These non-acidic impurities are typically produced during the process of synthesising the fatty acid, for example as described herein. Thus, the present invention typically does not involve separating fatty acids from one another.

Typically, the lithium salt is lithium bicarbonate, lithium carbonate or lithium hydroxide. Preferably, the lithium salt is lithium hydroxide, more preferably lithium hydroxide hydrate.

Typically, the fatty acid has 1 to 6 centers of unconjugated unsaturation as defined herein. Preferably the fatty acid is an ω-3 or ω-6 fatty acid.

Preferably the purification process occurs after the last of four synthetic stages:

Stage 1:

The lithium salt and crude fatty acid are combined in a first solution, and are held under conditions which allow formation of a precipitate of a lithium salt of the fatty acid. Suitable lithium salts include lithium bicarbonate, lithium carbonate and lithium hydroxide. Preferably the lithium salt is lithium hydroxide. The lithium salt may be supplied in the form of a hydrate, for example lithium hydroxide hydrate. It may be

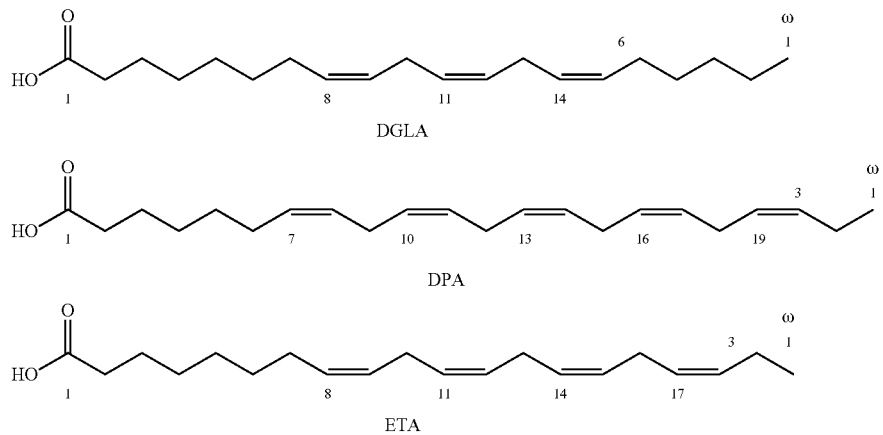

DGLA

DPA

ETA added to the first solution in its hydrate form, but is preferably first dissolved in a suitable solvent such as water. Preferably the first solution contains a ketone, more preferably acetone. The temperature of the reaction is preferably between about −30 and about 30° C.

Stage 2:

The precipitated lithium salt is then isolated. Any suitable method for isolating a solid precipitate from solution can be used, for example filtering. The precipitate is optionally washed with further solvent (e.g. the same solvent as in Stage 1, preferably acetone), and any solvent evaporated.

Stage 3:

The isolated precipitate is then dissolved in a second solution. The second solution is chosen such that, upon dissolution of the precipitate, two immiscible layers are formed. The two immiscible layers are a polar layer which is an aqueous acidic layer, and a non-polar, organic layer. The aqueous acidic layer is preferably an aqueous solution of a strong mineral acid such as hydrochloric acid. The non-polar, organic layer is suitably an ether A preferred ether for the non-polar layer is t-butyl methyl ether.

Stage 4:

In this stage the two immiscible layers formed upon dissolution of the precipitate are separated. Conventional separating techniques can be used, for example using a simple separating funnel. Following separation of the two immiscible layers, the resulting organic layer may optionally be washed with water and dried (e.g. using $Na_2SO_4$ followed by filtration).

Stage 5:

The solvent is removed from the organic layer by evaporation to isolate the purified fatty acid. The purified fatty acid has a higher level of purity compared to the crude product. For example, the purity can be increased by about 1% or greater, preferably about 2% or greater, more preferably about 5% or greater. The product obtained from this stage may be colourless or coloured. For example, a pale yellow oil can be obtained. The product is optionally further decolourised, suitably employing chromatographic silica in an appropriate solvent. For example, decolourisation can be achieved by stirring with 10-20% by weight chromatographic silica in hexane.

The crude fatty acid used in the above purification process can be derived from a number of sources. One suitable method for preparing the fatty acid is via decarboxylation of a malonic acid derivative. For example, a malonic acid derivative of formula $RCH_2CH(CO_2H)_2$ can be decarboxylated to form a fatty acid of formula $RCH_2CH_2CO_2H$. The resulting fatty acid of formula $RCH_2CH_2CO_2H$ can then be subjected to the purification process described above.

The malonic acid derivative described above can be derived from a number of sources. For example, it can be provided in crystalline form, having been isolated and optionally purified from an earlier process. However, it is preferably provided as a crude reaction product without having undergone purification. For example, it can be provided from reaction of a sulfonate to a malonic ester derivative, suitably via a malonic ester intermediate and subsequent hydrolysis.

The invention also provides a process for extending the length of a fatty acid. In particular, the process can be used to extend a fatty acid by two carbon atoms. The two carbon atoms are effectively inserted between the fatty acid residue R and the carboxylic acid group. The extension process comprises four separate stages:

Stage I

The starting fatty acid is of formula $R—CO_2H$. Alternatively, the corresponding fatty acid ester can be used, having formula $R—CO_2R^1$ wherein R is the fatty acid residue and $R^1$ is a $C_{1-6}$ alkyl group. Preferred $R^1$ groups are $C_{1-4}$ alkyl groups, more preferably methyl or ethyl, most preferably ethyl.

The fatty acid or fatty acid ester is reduced to form the corresponding fatty alcohol of formula $R—CH_2OH$. Suitable reduction techniques are well known, and skilled person will readily be able to choose appropriate reducing agents and reaction conditions. Reducing agents include Red-Al (sodium bis(2-methoxyethoxy)aluminumhydride), DIBAL (Di-isobutylaluminium hydride) and lithium aluminium hydride. The reducing agents are used in conjunction with an appropriate solvent, with suitable inert solvents including ethers and aromatic hydrocarbons and derivatives thereof. Preferred solvents include diethyl ether, tetrahydrofuran and toluene. The temperature of the reaction can vary, with a suitable temperature range being from 0 to 35° C. When the starting material is a fatty acid, then this reduction reaction evolves hydrogen. The hydrogen must be carefully and safely removed. Use of a fatty acid ester starting material reduces the amount of hydrogen liberated, as the only hydrogen produced results from decomposition of excess reducing agent.

The preferred reducing agent is lithium aluminium hydride. This can be added to the reaction in various forms, for example as a solid or in solution. Addition in solid form may be appropriate for small-scale production. For scaled-up processes it is preferred to employ lithium aluminium hydride in solution, leading to improved and safer handling.

Stage II

The alcohol prepared in Stage I is subsequently sulfonated to form a fatty acid sulfonate of formula $R—CH_2OSO_2R^2$, wherein $R^2$ is a $C_{1-6}$ alkyl or $C_{6-10}$ aryl group. Preferably $R^2$ is a $C_{1-6}$ alkyl, more preferably a $C_{1-4}$ alkyl, most preferably methyl. When $R^2$ is a $C_{6-10}$ aryl group, the aryl group is preferably phenyl. The aryl groups are unsubstituted or substituted, as described earlier. A most preferred substituent is methyl. Suitable sulfonating agents are chosen appropriately, for example methanesulfonyl chloride, phenylsulfonyl chloride and 4-methylphenylsulfonyl chlorides are preferred sulfonating agents, with methanesulfonyl chloride being particularly preferred. Preferably the reaction occurs in the presence of a tertiary base such as pyridine, 2,4,6-trimethylpyridine or triethylamine. The temperature of the reaction is preferably between about 0 and 40° C.

The reaction optionally occurs in a suitable solvent. Chlorinated solvents (e.g. dichloromethane) are conventionally used in this type of sulfonation reaction. However, minimisation or avoidance of the use of chlorinated solvent is preferred. One way to reduce or avoid use of a chlorinated solvent is to use pyridine as a base.

Stage III

The fatty acid sulfonate prepared in Stage II is subsequently reacted with a malonate ester derivative, the product thereof being hydrolysed to form a malonic acid derivative of formula $R—CH_2CH(CO_2H)_2$. The initial reaction preferably takes place in an anhydrous alcohol, for example absolute ethanol. The temperature of the reaction is preferably from about 60-90° C. The hydrolysis can take place under any suitable hydrolysis conditions, e.g. in aqueous alcohol in the presence of a group I metal hydroxide. The temperature of the reaction is preferably from about 15-50° C.

Suitable malonate ester derivatives are group I metalomalonates, including sodio dialkyl malonates, $NaCH(CO_2R^3)_2$ where $R^3$ a $C_{1-6}$ alkyl group. Preferably $R^3$ is a $C_{1-4}$ alkyl group, more preferably ethyl. The reaction initially produces an ester of formula $R—CH_2CH(CO_2R^3)_2$ which is then hydrolysed to prepare the malonic acid derivative of formula R—$CH_2CH(CO_2H)_2$. Hydrolysis reagents and conditions are well known. For example, reaction with a suitable hydroxide (e.g. sodium or potassium hydroxide) can yield the malonic acid derivative.

The malonic acid derivative of formula R—$CH_2CH(CO_2H)_2$ can, depending on the nature of R, be isolated and crystallised. However, some malonic acid derivatives do not crystallise easily or at all. For example, the malonic acid derivative formed from EPA or an ester thereof (i.e. where R is $H_3C$—$(CH_2$—$CH$=$CH)_5$—$(CH_2)_3$—) does not readily crystallise. In these circumstances, where a purification process cannot easily be performed on a non-crystallising product, the lithium salt purification process described above provides a convenient method for improving the purity of the final fatty acid. The lithium salt purification process avoids the need to crystallise and purify the malonic acid derivative of formula R—$CH_2CH(CO_2H)_2$, and instead allows purification of the final fatty acid product instead. Accordingly, the process for extending the length of a fatty acid described earlier preferably takes the crude product from Stage III and uses this as the feed for Stage IV, without first purifying the product of Stage III.

Stage IV

The malonic acid derivative prepared in Stage III is subsequently decarboxylated to form a fatty acid of formula R—$CH_2CH_2CO_2H$. Standard decarboxylation techniques can be used, with the evolved carbon dioxide being removed (e.g. by vacuum) during the course of the reaction. For example, simple heating can achieve decarboxylation. Suitable heating temperatures will vary, but general ranges include from 120-180° C., for example from 130-170° C., preferably from 140-160° C. The temperature should be held until the reaction has gone to completion, which will be apparent by the emission of carbon dioxide reducing and eventually ceasing. A vacuum can also be employed, for example a vacuum of less than about 30 mb is suitable.

Stage V

The fatty acid prepared in Stage IV is subsequently purified using the process for purifying a fatty acid as described above. Purification by this method removes non-acidic impurities from the fatty acid. The final fatty acid product has a higher level of purity compared to the fatty acid formed in Stage IV. The purity of the final fatty acid may have a purity similar to the purity of the initial fatty acid used in Stage 1, i.e. the fatty acid of formula R—$CO_2H$. If the initial fatty acid contained non-acidic impurities, then the purity of the final fatty acid will be greater.

EXAMPLES

Example 1

Preparation and Purification of DGLA
(Icosa-8(Z),11(Z),14(Z)-trienoic acid

Example 1a

Preparation of GLAlcohol
(Octadeca-6(Z),9(Z),12(Z)-trienol)

To dry fresh tetrahydrofuran (12000 parts, vol) under nitrogen is added lithium aluminium hydride in tetrahydrofuran (2.4 Molar, 1620 parts, vol). The mixture is cooled to 0-5° C. and GLA (gamma linolenic acid, 95-98%, 1112 parts, wt) in dry tetrahydrofuran (2000 parts, vol) is added over 30-40 min, keeping the temperature at around 3-7° C., with stirring and under a nitrogen stream. The mixture is then stirred at 8-12° C. for 1 hr and 12-18° C. for 2 hr under nitrogen. After cooling to 3-5° C., a solution of water (152 parts, vol) in tetrahydrofuran (500 parts, vol) is added under a good stream of nitrogen over 15-20 min. An aqueous solution of sodium hydroxide (2 M, 456 parts, vol) is then added over 10-15 min. The mixture is stirred at 10-15° C. sealed under nitrogen overnight and then anhydrous sodium sulfate (500 parts, wt) is added and the mixture stirred for a further 30 min. After filtration, the inorganic solids are washed with tetrahydrofuran (2000 parts, vol). The resulting THF solution is evaporated under vacuum. Any water in the product is removed by evaporating with 2×2000 parts, vol. of toluene. There is obtained GLAlcohol (1029 parts, wt, 97.4%) as a pale yellow oil.

Example 1b

Preparation of GLAlcohol Methane Sulfonate
(Octadeca-6(Z),9(Z),12(Z)-trienyl methane sulfonate To a stirred mixture of GLAlcohol (1000 parts, wt) and methanesulfonyl chloride (456 parts, wt) under nitrogen and at 8-12° C. is added dry pyridine (307 parts, wt) over a period of 30-40 min keeping the temperature below 15° C. The mixture is stirred at this temperature for 3-5 hrs and then allowed to warm up to room temperature and stirred over a period of 24-48 hrs. A precipitate of pyridine hydrochloride occurs in the mixture. The reaction mixture is then diluted with hexane (4000 parts, vol), anhydrous sodium sulfate (200 parts, wt) added and the resulting mixture stirred for 1 hr. The precipitated solids are filtered off and washed with hexane. The hexane is removed from the filtrate in vacuo to give the crude methane sulfonate (1300 parts, wt) which can be used for the next stage.

An alternative purification method (resulting in a purer product and a less coloured final product of the later stages) is as follows: The reaction mixture is diluted with t-butyl methyl ether (4000 parts, vol) and cooled to 5-10° C. With stirring and under nitrogen, water (2000 parts, vol) is added and the aqueous layer adjusted to pH=1-2 with concentrated hydrochloric acid. After 15 min., the layers are separated and the aqueous layer extracted with t-butyl methyl ether (500 parts, vol). The combined organic layers are then washed with 1M hydrochloric acid (1000 parts, vol) and water (4×500 parts, vol.). The organic layer is dried (anhydrous sodium sulfate, 300 parts, wt), filtered and evaporated in vacuo to give purer methane sulfonate to use for the next stage.

Example 1c

Preparation of 2-Carboxy DGLA (2-Carboxy-icosa-8
(Z),11(Z),14(Z)-trienoic acid

To absolute ethanol (10000 parts, vol) was added sodium methoxide 30% w/v in methanol (1370 parts, vol). At room temperature under nitrogen, diethyl malonate (1520 parts, wt) is added in a fast stream over 10-15 min. and the mixture is stirred for a further 10-15 min. Crude GLAlcohol methane sulfonate (1300 parts) is added in a fast stream over 10-15 min and the mixture is stirred and heated under reflux for 3.5-4.0 hrs. under nitrogen. After cooling to room temperature, a solution made by dissolving potassium hydroxide 85% (1900 parts, wt,) in water (1000 parts, vol) and then adding 95% ethanol (13000 parts, vol), is added under nitrogen. An exotherm occurs and the temperature of the reaction reaches 30-40° C. The mixture is stirred at room temperature for 4-5 hrs. under nitrogen. The total reaction mixture is evaporated in the rotary evaporator to remove the ethanol. The residue from the evaporation is dissolved in water (10000 parts, vol) and t-butyl methyl ether (10000 parts, vol) was added. The mixture is stirred and acidified under nitrogen using 20% sulfuric acid (approx. 6000 parts, vol) (Max temp. 20° C.). After separating the layers, the organic layer is washed with water (4×2000 parts, vol), dried (anhydrous sodium sulfate) and evaporated in vacuo to give an oil which crystallises on scratching to give crude 2-Carboxy DGLA (1170-1220 parts, wt, 88-92%).

Example 1d

Preparation of DGLA
(Icosa-8(Z),11(Z),14(Z)-trienoic acid

Crude 2-Carboxy DGLA (1200 parts, wt) is heated with stirring under a vacuum of <30 mb at 140-160° C. Carbon dioxide is evolved and is removed by the vacuum. After 3-5 hrs, the emission of carbon dioxide ceases. The flask is cooled to room temperature and nitrogen is let into the reaction vessel to give an oil (1000-1030 parts, wt, 95-98%).

Example 1e

Purification of DGLA

The product of Example 1d (1000 parts, wt) is dissolved in HPLC (or equivalent) acetone (3550-3600 parts, vol) and with good stirring and under nitrogen, a solution of lithium hydroxide hydrate (150 parts, wt.) in water (975 parts, vol) is added slowly over 30 min. The mixture is stirred for a further 10 min. Further acetone (3500-3600 parts, vol) is added over 30 minutes with stirring and stirring is continued with cooling to 0 to −5° C. over a period of 2-3 hrs. The mixture is allowed to stir overnight at this temperature. The precipitated lithium salt is filtered and washed with pre-cooled acetone and sucked dry. The resulting solid is added in portions to a stirred cooled (0-10° C.) mixture of t-butyl methyl ether (6000 parts, vol) and 1M hydrochloric acid (6000 parts, vol) under nitrogen. The resulting organic layer is separated, washed with water (4×500-750 parts, vol) and dried ($Na_2SO4$). After filtration, the solvent is evaporated and the resulting oil is heated under high vacuum (50-60° C., 0.1-1.0 mb) for several hrs to remove traces of solvent. There is obtained DGLA as a pale yellow oil (760-800 parts, wt, 76-80%). Decolourisation to a clear oil can be obtained by stirring the DGLA in 10 volumes of hexane in the presence of chromatographic silica 35-70 µm particle size (20% by wt.) for 1 hr., filtering and evaporating the solvent Example 2

Preparation and Purification of DPA (Docosa-7(Z), 10(Z),13(Z),16(Z),19(Z)-pentaenoic acid DPA was prepared in the same was as DGLA in Example 1 but from the starting material EPA ethyl ester (ethyl ester of eicosapentaenoic acid).

In a first step, EPAlcohol (Icosa-5(Z),8(Z),11(Z),14(Z),17(Z)-pentaenol) was formed in a similar manner to Example 1a by replacing the GLA with EPA ethyl ester (1320 parts, wt).

In a second step, EPAlcohol methane sulfonate (Icosa-5(Z),8(Z),11(Z),14(Z),17(Z)-pentaenyl methane sulfonate) was formed in a similar manner to Example 1b by replacing the GLAlcohol with said EPAlcohol (1091 parts, wt).

In a third step, 2-Carboxy DPA (2-Carboxy-docosa-7(Z), 10(Z),13(Z),16(Z), 19(Z)-pentaenoic acid) was formed in a similar manner to Example 1c by replacing the GLAlcohol methane sulfonate with the said EPAlcohol methane sulfonate (1391 parts, wt).

In a fourth step, DPA (Docosa-7(Z),10(Z),13(Z),16(Z),19(Z)-pentaenoic acid) was formed in a similar manner to Example 1d by replacing the 2-Carboxy DGLA with the said 2-Carboxy DPA with cooling of the acetone mixture to −15 to −20° C.

In a fifth step, the DPA is purified using the same lithium salt purification method of Example 1e but replacing the DGLA with said DPA.

The invention claimed is:

1. A process for purifying a fatty acid which has 1 to 6 centers of unconjugated unsaturation, which process comprises:
   (a) reacting a fatty acid with a lithium salt in a first solution and under conditions to allow formation of a precipitate of a lithium salt of the fatty acid;
   (b) isolating the precipitate;
   (c) dissolving the precipitate in a second solution which is capable of generating two immiscible layers upon dissolution of the precipitate, the two immiscible layers being an organic layer and an aqueous acidic layer;
   (d) separating the two immiscible layers formed upon dissolution of the precipitate; and
   (e) evaporating the organic layer to isolate the purified fatty acid,
   wherein the process does not involve separating fatty acids from one another.

2. A process according to claim 1 wherein the fatty acid is selected from the group consisting of dihomo-gamma-linolenic acid (DGLA), eicosadienoic acid, docosapentaenoic acid (DPA), eicosatetraenoic acid (ETA) and eicosatrienoic acid.

3. A process according to claim 1 wherein the fatty acid is a $C_{14-24}$ fatty acid.

4. A process according to claim 1 wherein the lithium salt is lithium hydroxide.

5. A process for preparing a fatty acid which has 1 to 6 centers of unconjugated unsaturation, which process comprises:
   (a) decarboxylating a malonic acid derivative of formula R—$CH_2CH(CO_2H)_2$, wherein R is a fatty acid residue which contains from 1 to 6 centers of unconjugated unsaturation, to form a fatty acid of formula R$CH_2CH_2CO_2H$;
   (b) subjecting the fatty acid thus prepared to a process for purifying a fatty acid as defined in claim 1.

6. A process for extending the length of a fatty acid which has 1 to 6 centers of unconjugated unsaturation, which process comprises:
   (a) reducing a fatty acid of formula R—$CO_2H$ or a fatty acid ester of formula R—$CO_2R^1$, wherein R is a fatty acid residue which contains from 1 to 6 centers of unconjugated unsaturation and $R^1$ is a $C_{1-6}$ alkyl group, to an alcohol of formula R—$CH_2OH$;
   (b) sulfonating the alcohol to form a sulfonate of formula R—$CH_2OSO_2R^2$, wherein $R^2$ is a $C_{1-6}$ alkyl or $C_{6-10}$ aryl group;
   (c) reacting the sulfonate with a malonate ester derivative and hydrolysing the resulting product to form a malonic acid derivative of formula R—$CH_2CH(CO_2H)_2$;
   (d) decarboxylating the malonic acid derivative to form a fatty acid of formula R—$CH_2CH_2CO_2H$; and
   (e) subjecting the fatty acid thus prepared to a process for purifying a fatty acid as defined in claim 1.

7. A process according to claim 6 wherein R is a fatty acid residue comprising from 14 to 22 carbon atoms.

8. A process according to claim 7 wherein R comprises from 18 to 20 carbon atoms.

9. A process according to claim 6 wherein R comprises 2 to 6 unconjugated olefinic groups.

10. A process according to claim 6 wherein R is selected from the group consisting of ω-3 and ω-6 fatty acid residues.

11. A process according to claim 6 wherein R is selected from the group consisting of a $C_{17}H_{29}$ residue from gamma-linolenic acid, a $C_{19}H_{29}$ residue from eicosapentaenoic acid, a $C_{17}H_{27}$ residue from stearidonic acid, a $C_{17}H_{31}$ residue from linoleic acid and a $C_{17}H_{29}$ residue from alpha-linolenic acid.

12. A process according to claim 6 wherein the reduction in step (a) is carried out with a solution of lithium aluminium hydride.

13. A process according to claim 6 wherein the malonic acid derivative of formula $R-CH_2CH(CO_2H)_2$ is used directly in the decarboxylation of step (d) without purification and/or without crystallisation.

14. A process according to claim 5 wherein R is a fatty acid residue comprising from 14 to 22 carbon atoms.

15. A process according to claim 14 wherein R comprises from 18 to 20 carbon atoms.

16. A process according to claim 5 wherein R comprises 2 to 6 unconjugated olefinic groups.

17. A process according to claim 5 wherein R is selected from the group consisting of ω-3 and ω-6 fatty acid residues.

18. A process according to claim 5 wherein R is chosen from the group consisting of a $C_{17}H_{29}$— residue from gamma-linolenic acid, a $C_{19}H_{29}$— residue from eicosapentaenoic acid, a $C_{17}H_{27}$— residue from stearidonic acid, a $C_{17}H_{31}$— residue from linoleic acid and a $C_{17}H_{29}$— residue from alpha-linolenic acid.

\* \* \* \* \*